ary, or Firm—Jacobs & Jacobs

United States Patent [19]

Pearson et al.

[11] 4,108,992
[45] Aug. 22, 1978

[54] CEPHALOSPORIN ANALOGUES AND COMPOSITIONS

[75] Inventors: Michael John Pearson, Roffey; Clive Leslie Branch, South Holmwood, both of England

[73] Assignee: Beecham Group Limited, Great Britain

[21] Appl. No.: 766,213

[22] Filed: Feb. 7, 1977

Related U.S. Application Data

[62] Division of Ser. No. 684,078, May 7, 1976.

[30] Foreign Application Priority Data

May 10, 1975 [GB] United Kingdom ............... 19744/75

[51] Int. Cl.² ......................... A01N 9/00; A01N 9/22; C07D 265/00; C07D 273/00
[52] U.S. Cl. ........................ 424/248.53; 424/248.54; 544/90
[58] Field of Search ............... 260/244 R; 424/248.53, 424/248.54, 248.55, 248.56; 544/90

[56] References Cited

U.S. PATENT DOCUMENTS

| 3,728,342 | 4/1973 | Kukolja .......................... 260/243 C |
| 3,769,277 | 10/1973 | Long et al. ..................... 260/243 C |
| 3,795,672 | 3/1974 | Murphy ........................... 260/243 C |
| 4,011,216 | 3/1977 | Menard et al. ................. 260/244 R |
| 4,013,648 | 3/1977 | Horning et al. ................ 260/244 R |
| 4,013,653 | 3/1977 | Wolfe ............................... 260/244 R |

FOREIGN PATENT DOCUMENTS

| 1,914,366 | 10/1970 | Fed. Rep. of Germany. |
| 2,355,209 | 3/1974 | Fed. Rep. of Germany. |
| 2,355,210 | 3/1974 | Fed. Rep. of Germany. |

OTHER PUBLICATIONS

J. Heterocyclic Chem. 5, 779–783, 1968–Sheehan et al., "The Synthesis of Oxygen Analogs of Cepham".

Primary Examiner—Albert T. Meyers
Assistant Examiner—D. W. Robinson
Attorney, Agent, or Firm—Jacobs & Jacobs

[57] ABSTRACT

Novel cephalosporin analogues, salts and esters thereof, their preparation, intermediates and antibacterial compositions containing them. The compositions are formulated for human use into unit dosage form containing 100–4,000 mg of antibacterial compound. The cephem analogues are characterized by having a ring O-heteroatom instead of a ring N-heteroatom and are designated as oxacephems.

12 Claims, No Drawings

CEPHALOSPORIN ANALOGUES AND COMPOSITIONS

This is a division of Ser. No. 684,078 filed May 7, 1976.

The present invention relates to novel cephalosporin analogues, to the process for their preparation and to antibacterial compositions containing them.

The present invention provides compounds of the formula (I):

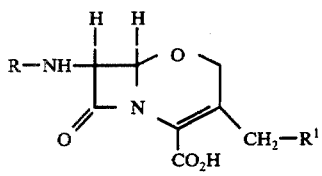
(I)

and their salts and in vivo hydrolysable esters wherein R is an acyl group as found in known penicillins and cephalosporins and $R^1$ is a hydrogen atom or an organic group containing 1 to 10 carbon atoms.

Examples of acylamino groups known to be suitable for inclusion in known penicillins and cephalosporins include those of the sub-formulae (a) – (d):

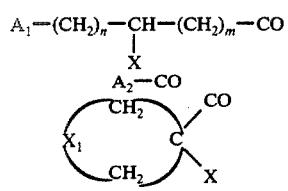

$A_2 — X_2 — (CH_2)_n — CO$ (d)

wherein $n$ is 0, 1 or 2; $m$ is 0, 1 or 2; $A_1$ is $C_1$-$C_6$ alkyl, $C_3$-$C_6$ cycloalkyl, cyclohexenyl, cyclohexadienyl, phenyl, hydroxy phenyl, thienyl or pyridyl group; X is a hydrogen or halogen atom, a carboxylic acid, carboxylic ester, azido, tetrazolyl, hydroxy, acyloxy, amino, ureido, guanidino or acylureido group; $A_2$ is a bulky aromatic group such as a 2,6-dimethoxyphenyl, 2-alkoxy-1-naphthyl, 3-arylisoxazolyl or 3-aryl-5-methylisoxazolyl group; $X_1$ is a $CH_2OCH_2$, $CH_2SCH_2$ or $(CH_2)_n$ group; $X_2$ is an oxygen or sulphur atom.

When used in relation to formula (I) the term "salt" includes acid addition salts of those compounds containing amino groups as well as salts of any carboxylic acid groups present. Such salts are preferably pharmaceutically acceptable salts such as the sodium, potassium, calcium, magnesium, aluminium, ammonium and conventional substituted ammonium salts.

Examples of suitable organic groups $R^1$ include those found in known cephalosporins or cephalosporin analogues and include those of the sub-formulae (e) – (i):

$—CHA^3A^4$ (e)

(f)

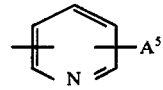
(g)

$—O—CO—A^6$ (h)

$—S—A^7$ (i)

wherein $A^3$ is a hydrogen atom or a lower alkyl group; $A^4$ is a hydrogen atom or a lower alkyl group; $A^5$ is a hydrogen atom or a lower alkyl, ester, carboxamide or optionally salted carboxylic acid group; $A^6$ is a methyl or amino group and $A^7$ is a 5- or 6-membered heteroaromatic group which contains at least one nitrogen atom.

Examples of suitable in vivo hydrolysable esters of the compounds of this invention include those which break down readily in the human body to leave the parent acid, e.g. acyloxyalkyl esters such as acetoxymethyl, pivaloyloxymethyl, α-acetoxyethyl, α-acetoxybenzyl and α-pivaloyloxymethyl esters. Other suitable esters include lactone, esters of the sub-formula (j):

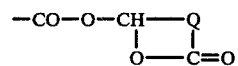
(j)

wherein Q is a divalent hydrocarbon group, especially the phthalidyl and substituted phthalidyl esters such as the 6,7-dimethoxyphthalidyl ester.

One group of suitable compounds of this invention are those of the formula (II):

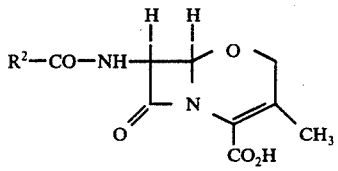
(II)

and pharmaceutically acceptable salts thereof wherein $R^2$ is a group of the sub-formulae (k) or (l):

$A^8 — Q^1 — CH_2 —$ (k)

$A^9 — CHQ^2 —$ (l)

wherein $A^8$ is a phenyl, thienyl or pyridyl group; $Q^1$ is an oxygen or sulphur atom or a bond joining $A^8$ to the methylene group; $A^9$ is a phenyl, p-hydroxyphenyl or thienyl group; and $Q^2$ is a hydroxy, amino, carboxylic acid or $C_{1-10}$ esterified carboxylic acid group.

Further suitable groups of compounds of this invention are those of the formulae (III) and (IV):

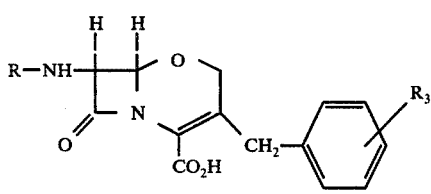
(III)

-continued

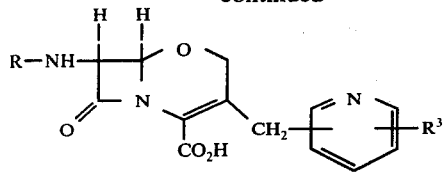
(IV)

and pharmaceutically acceptable salts thereof wherein R is as defined in relation to the formula (I) and $R^3$ is a hydrogen atom or a carboxylic acid, carboxamido group or $C_{1-10}$ esterified carboxylic acid group.

In compounds of the formula (III) and (IV) R is most suitably a group of the sub-formulae (k) or (l) as defined in relation to formula (II).

A particularly suitable group R for inclusion in the compounds of formula (I), (III) and (IV) is the D-mandelyl group.

The present invention also provides antibacterial pharmaceutical compositions which comprise a compound of the formula (I) together with a pharmaceutically acceptable carrier.

The compositions of this invention are normally adapted for administration to humans. Such compositions may be formulated in a conventional manner for antibacterial agents, for example, in a similar manner to known penicillins or cephalosporins. Unit dose formulations according to this invention will normally contain from 100 mg. to 4000 mg., more usually from 125 mg. to 1000 mg. and generally from 250 mg. to 500 mg. of a compound of the formula (I).

Compounds of the formula (I) and their salts may be prepared by the N-acylation of a compound of the formula (V):

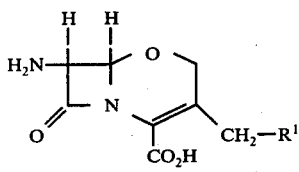
(V)

or a salt, ester or silyl derivative thereof with an acylating derivative of a carboxylic acid ROH and thereafter removing any silyl or ester group present.

Silyl groups may be removed by hydrolysis or alcoholysis in conventional manner. Ester groups may be removed by hydrolysis, by treatment with anhydrous acid or by hydrogenolysis in conventional manner. If it is desired to form an in vivo hydrolysable ester of the compound of formula (I) then the appropriate ester of the compound (V) or its silyl derivative may be acylated and any silyl group removed in conventional manner thereafter. Alternatively, a compound of the formula (I) or a salt thereof may be esterified in conventional manner.

The term "acylating derivative of a carboxylic acid" means any N-acylating compound known to be suitable for the performance of analogous reactions with 6-aminopenicillanic acid, 7-aminocephalosporanic acid, 7-aminodesacetoxycephalosporanic acid or their salts, silyl derivatives or esters. Reactive groups present in such acylating agents may be protected in conventional manner as will be well understood by those skilled in the arts of preparing semi-synthetic penicillins or cephalosporins.

Compounds of the formula (I) and their salts and in vivo hydrolysable esters wherein neither the R.NH nor the $CH_2R^1$ side chains carry reactive substituents may also be prepared by heating an ester of a compound of the formula (VI):

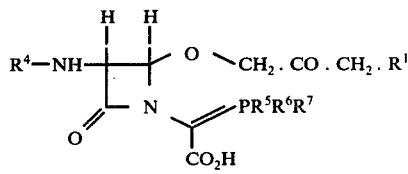
(VI)

wherein $R^4$ is an acyl group which does not carry any reactive substituents and $R^5$, $R^6$ and $R^7$ are inert hydrocarbon groups of 1–7 carbon atoms, and thereafter removing the ester group in conventional manner if desired.

Suitably $R^5$, $R^6$ and $R^7$ are methyl, ethyl, phenyl, benzyl, tolyl or like inert groups and preferably each of $R^5$, $R^6$ and $R^7$ are phenyl groups.

Most suitably the ring closure is effected at a temperature of 30°–170° C in a non-hydroxylic solvent.

If the group $R^1$ present in the compound of the formula (V) contains reactive moieties such moieties are normally reversably protected during the above described ring closure and regenerated at a convenient later stage.

Esters of the compound of the formula (V) may be prepared by the removal of a conventional N-protecting group from an ester of a compound of the formula (VII):

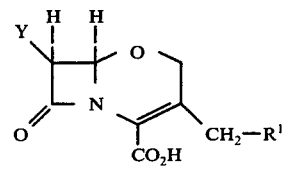
(VII)

wherein Y is a protected amino group or a group $R^4$-NH as hereinbefore described.

By "protected amino group" we mean an amino group substituted by a removable substituent which renders the amino group inert to reaction with a $CH_2CO.CH_3$ or esterified $R^5R^6R^7P=C(CO_2H)-$ group. Typical protected amino groups include the tritylamino and phthalimido group.

We have preferred to use esters of the compound of formula (VII) wherein Y is a $Ph_3C.NH$ group, as this group is readily converted to a salted amino group by reaction with an anhydrous acid, for example, by treatment with p-toluenesulphonic acid in organic solvent. The free amino group may then be obtained by neutralisation.

Esters of compounds of the formula (VII) may be prepared by heating an ester of a compound of the formula (VIII):

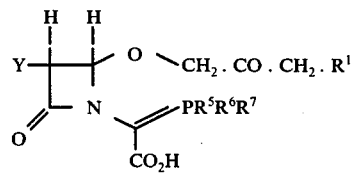
(VIII)

wherein Y is as defined in relation to formula (VII) and $R^1$, $R^5$, $R^6$ and $R^7$ are defined in relation to formula (VII).

Most suitably the ring closure in effected at a temperature of 30°–170° C in a non-hydroxylic solvent.

Esters of the compounds of the formula (VIII) may be prepared by reaction of $PR^5R^6R^7$ with the corresponding ester of a compound of the formula (IX):

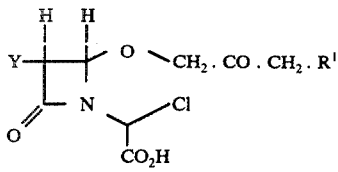

wherein $R^5$, $R^6$, $R^7$, $R^1$ and Y are as defined in relation to formula (VIII).

The preceeding reaction may be carried out in an inert solvent such as tetrahydrofuran or dioxan which also contains at least one equivalent of a base such as lutidine to remove the HCl liberated during the reaction. Normally, the reaction is carried out at a slightly elevated temperature, for example, 25°–60° C.

Esters of the compounds of the formula (IX) may be prepared by the reaction of a chlorinating agent such as thionyl chloride on the esters of the corresponding compound of the formula (X):

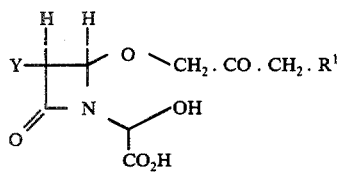

wherein Y and $R^1$ are as defined in relation to formula (IX).

This reaction may be carried out in an inert solvent such as tetrahydrofuran or dioxan which also contains at least one equivalent of a base such as lutidine to remove the HCl formed during the reaction. Normally the reaction is carried out at a depressed temperature for example, −20°–5° C.

The esters of the compound of formula (X) may be prepared by the reaction of a corresponding ester of glyoxylic acid with a corresponding compound of the formula (XI):

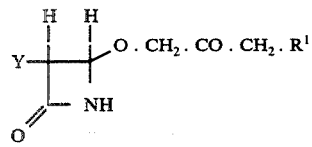

wherein $R^1$ and Y are as defined in relation to formula (X).

The preceeding reaction may be carried out in an inert solvent such as benzene under conditions which lead to the removal of the water formed during the reaction. Normally the reaction is carried out at an elevated temperature, for example, at the reflux point of the reaction mixture.

An alternative method of preparing the esters of the compound of the formula (X) comprises the ozonolysis of an ester of compound of the formula (XII):

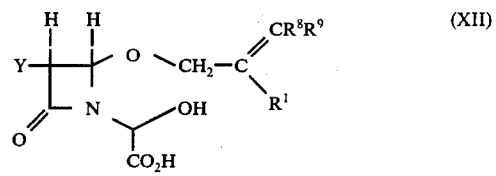

wherein Y and $R^1$ are as defined in relation to formula (X) and $R^8$ and $R^9$ are hydrogen atoms or organic radicals of 1–10 carbon atoms.

Suitably $R^8$ is a hydrogen atom and $R^9$ is an alkyl group of 1–4 carbon atoms or $C_{1-8}$ esterified carboxyl group. Most suitably $R^9$ is a methoxycarbonyl group.

The ozonolysis reaction may be carried out in an inert solvent such as ethyl acetate at a depressed temperature, for example, below −50° C. Normally ozonised oxygen is passed through the reaction solution until no starting material remains.

The compound of the formula (XI) may be prepared by the ozonolysis of a compound of the formula (XIII):

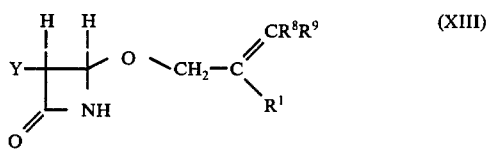

wherein $R^1$, $R^8$, $R^9$ and Y are as defined in relation to formula (XII). This reaction may proceed under the conditions outlined for the ozonolysis of a compound of the formula (XII).

Esters of the compound of formula (XII) may be prepared by the reaction of the corresponding glyoxylate ester with a compound of the formula (XIII). This reaction may proceed under the conditions outlined for the reaction of a glyoxylate ester with a compound of the formula (XI).

The compound of the formula (XIII) may be prepared by the reaction of an alcohol of the formula (XIV):

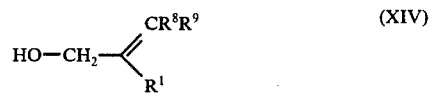

with an azetidinone of the formula (XV):

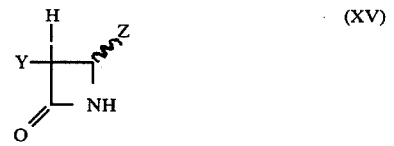

wherein Y is as defined in relation to formula (XIV) and Z is a $O.CO.CH_3$ or $SO_2CH_3$ group.

The preceeding reaction may be carried out in an inert solvent such as toluene at an elevated temperature, for example, 60°–100° C, in the presence of a catalyst such as zinc acetate dihydrate. This reaction leads to a mixture of the cis- and trans- isomers from which the desired cis- isomer may be obtained by chromatography, for example, on silica gel using ethyl acetate as eluent.

The esters of the compounds of the formulae (VIII) wherein $R^1$ is a hydrogen atom may be prepared by the hydration of esters of a corresponding acetylene of the formula (XVI):

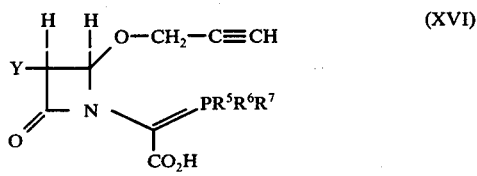

wherein $R^5$, $R^6$, $R^7$ and Y are as defined in relation to formula (VIII).

The preceeding reaction may be carried out in a basic solvent such as piperidine at ambient temperature. Most suitably the reaction mixture contains a mercuric salt such as mercuric chloride as catalyst.

Compounds of the formula (XVII):

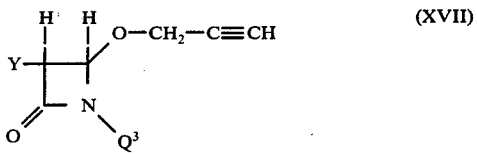

wherein $Q^3$ is an esterified $CH(CO_2H)Cl$ or $CH(CO_2H)OH$ group may be prepared via the compound of the formula (XVII) wherein $Q^3$ is hydrogen using the conditions outlined for the preparation of the esters of the compounds of the formulae (IX) and (X).

The compounds of the formula (XVII) wherein $Q^3$ is a hydrogen atom may be prepared by the reaction of propargyl alcohol with a compound of the formula (XV) under conditions similar to those already described for the preparation of the compounds of the formula (XVII).

The compounds of the formula (XV) wherein Z is an OCOCH$_3$ group may be prepared by the method of Stoodley et al., J.C.S. Perkin, 32 (1973) followed by oxidative removal of the N— substituent. The compounds of the formula (XV) wherein Z is a SO$_2$CH$_3$ group may be prepared by the oxidation of compounds of the formula (XV) wherein Z is SCH$_3$, themselves prepared by the method of Brain et al., J.C.S. Chem. Comm., 229 (1972).

The useful novel intermediates of the formulae (V)–(XIII) form a part of this invention. The process for the preparation of the compounds of the formulae (I)–(XIII) form a part of this invention.

The present invention is illustrated by the following Examples:

EXAMPLE 1(A)

(3S,4S)-4-Acetoxy-1-(1'-methoxycarbonyl-2'-methyl-prop-1'-enyl)-3-phenoxyacetamidoazetidin-2-one (2)

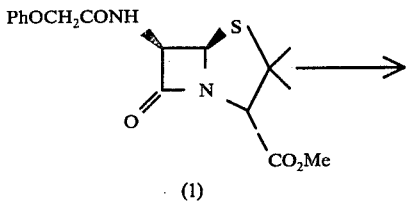

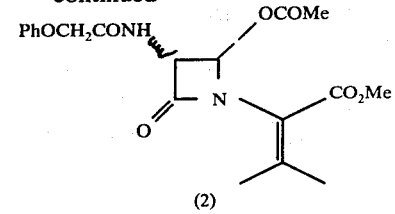

Phenoxymethylpenicillin methyl ester (1) (20.3 g) was heated to 95° with mercury (II) acetate (36.3 g) in glacial acetic acid (250 ml). The cooled mixture was filtered to remove mercury (I) acetate, and the filtrate was evaporated on the water-pump. The residue was taken up in ethyl acetate and the solution washed with aqueous sodium bicarbonate. The mixture was filtered through kieselguhr to remove precipitated solid; and the organic layer was separated, washed with brine, dried and evaporated. Chromatography on silica H afforded the crystalline product (2; 14.9) m.p. 161° (ethyl acetate/petroleum ether). $\nu_{max}$ (CHCl$_3$) 3320, 1780, 1760 (sh), 1690, 1630 cm$^{-1}$. $\delta$ ppm (CDCl$_3$) 2.02 (s, 3H), 2.1 (s, 3H), 2.24 (s, 3H), 3.79 (s, 3H), 4.56 (s, 2H), 5.11 (d.d., 1H, J=1.5 Hz and 8 Hz), 6.27 (d, 1H, J=1.5 Hz), 6.83–7.45 (m, 5H), 7.6 (d, 1H, J=8Hz). (Found:- C, 58.42; H, 5.74; N, 6.93% $C_{19}H_{22}N_2O_7$ requires C, 58.46; H, 5.64; N, 7.17%).

EXAMPLE 1(B)

(3S,4S)-4-Acetoxy-3-phenoxyacetamidoazetidin-2-one (3)

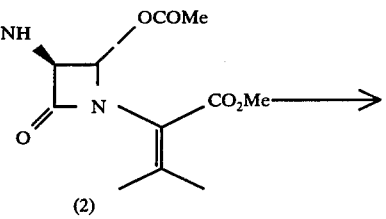

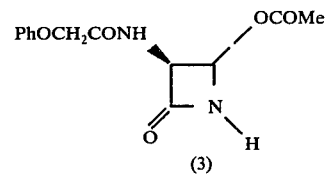

The lactam (2; 15.6g) was dissolved in DMF/pyridine/water (250 ml: 250 ml:50 ml) and the solution cooled to $-20°$. Powdered potassium permanganate (9.48 g) was added in portions over 10 minutes and the mixture stirred at $-20°$ for a further 2 hours. Ethyl acetate was added and sulphur dioxide was passed through the cooled mixture until all the manganese dioxide had been removed. The mixture was washed with dilute hydrochloric acid, until the aqueous layer was acidic, then dilute aqueous sodium bicarbonate and brine. The organic layer was separated, dried and evaporated. The product was recrystallised from ethylacetate/petroleum ether to afford the azetidinone (3; 5.56 g) m.p. 144°–145°. $\nu_{max}$ (CHCl$_3$) 3370, 1793, 1745, 1690, 1600 cm$^{-1}$. $\delta$ ppm (CDCl$_3$) 2.12 (s, 3H), 4.53 (s, 2H), 5.0 (d.d., 1H, J=2 Hz and 9 Hz, collapsing to a doublet J=2 Hz on D$_2$O exch.), 5.95 (d, 1H, J=2 Hz), 6.8–7.6 (m, 6H), 7.73 (d, 1H, J=9Hz, exchanges with D₂O). (Found:- C, 55.96; H, 5.33; N, 10.33%: C₁₃H₁₄N₂O₅ requires C, 56.11; H, 5.04; N, 10.07%).

EXAMPLE 1(C)

(3R, 4S)-3-Phenoxyacetamido-4-(propargyloxy)azetidin-2-one (4) and (3S, 4S)-3-Phenoxyacetamido-4-(propargyloxy)azetidin-2-one (5)

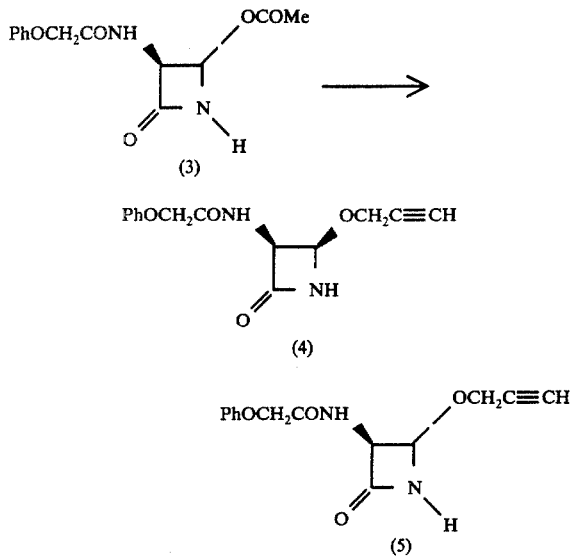

The trans-acetate (3; 2.78 g), propargyl alcohol (1.68 g), and zinc acetate dihydrate (1.1 g) were stirred at 80° in toluene for 3½ hours. The mixture was filtered and the filtrate evaporated. Chromatography of the residue on silica G afforded the trans-isomer (5; 430 mg) m.p. 149° (ethyl acetate/petroleum ether), $\nu_{max}$ (Nujol) 3310, 3250, 3180, 2100, 1780, 1765, 1680 cm⁻¹ δ ppm (CDCl₃ + D₆DMSO) 2.6 (t, 1H, J=2Hz), 4.35 (d, 2H, J=2 Hz), 4.58 (s, 2H), 4.77 (d.d, 1H, J=1.5 Hz and 8 Hz), 5.28 (d, 1H, J=1.5 Hz), 6.9–7.6 (m, 5H), 7.93 (d, 1H, J=8 Hz), 8.13 (s, 1H, exchanged with D₂O). (Found:- C, 61.10; H, 5.24; N, 9.79%; C₁₄H₁₄N₂O₄ requires C, 61.30; H, 5.11; N, 10.22%).

Further elution of the column provided the cis-isomer (4; 414 mg). mp. 96° (ethyl acetate/petroleum ether) $\nu_{max}$(CHCl₃) 3340, 3230, 1780, 1690 cm⁻¹. δ ppm (CDCl₃) 2.55 (t, 1H, J=2Hz), 4.27 (d, 2H, J=2Hz), 4.6 (s, 2H), 5.4 (d, 1H, J=4Hz), 5.57 (d.d, 1H, J=4 Hz and 8 Hz), 6.9–7.7 (m, 7H). (Found:- C, 61.13; H, 5.55; N, 10.13%; C₁₄H₁₄N₂O₄ requires C, 61.30; H, 5.11; N, 10.22%).

EXAMPLE 1 (D)

(3R,4S)-1-1'-Hydroxy-1'-tert-butoxycarbonylmethyl)-3-(phenoxyacetamido)-4-(propargyloxy)azetidin-2-one (6)

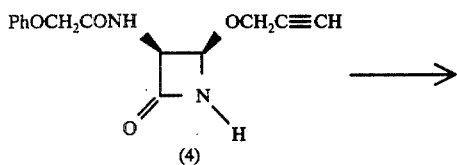

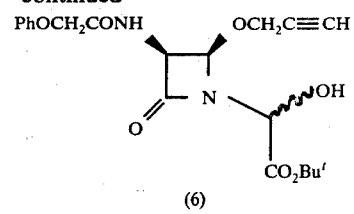

Tert-butylglyoxylate hydrate (1.48 g) was refluxed in benzene (6 ml) in a Dean-Stark apparatus to remove any water present and then the azetidinone (4; 274 mg) was added in benzene (4 ml). The mixture was refluxed for one hour. The cooled benzene solution was washed five times with water and once with brine, dried (MgSO₄) and evaporated to an oil which was chromatographed on silica G. The product (6) was an amorphous solid (244 mg) $\nu_{max}$ (CHCl₃) 3340, 3225, 2100, 1780, 1730, 1690 cm⁻¹.

EXAMPLE 1 (E)

(3R, 4S)-1-(1'-t-Butoxycarbonyl-1'-triphenylphosphoranylidenemethyl)-3-(phenoxyacetamido)-4-(propargyloxy)azetidin-2-one (8)

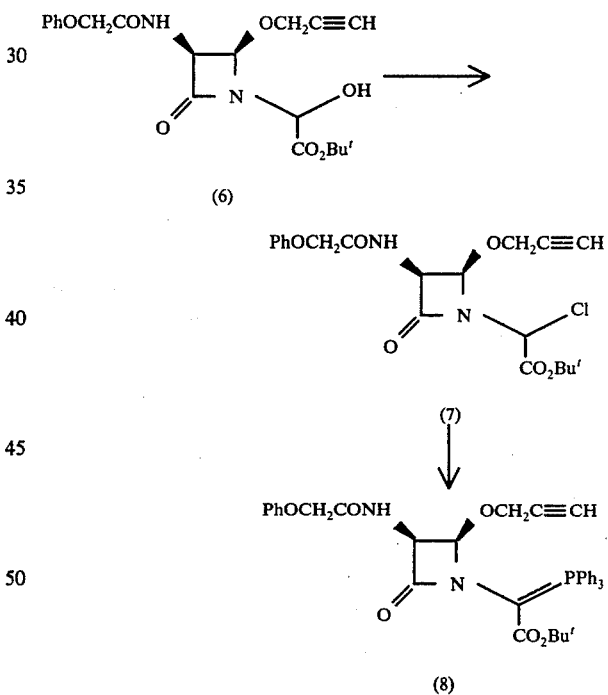

The hydroxy-compound (6; 208 mg) was dissolved in dry tetrahydrofuran (3 ml) and the solution cooled to −15°. Lutidine (107 mg) was added followed by the dropwise addition of thionyl chloride (119 mg) in dry tetrahydrofuran (0.5 ml). After 20 minutes the solution was filtered to remove the precipitated lutidine hydrochloride, and the filtrate was evaporated and dried in vacuo to give (7) as an amorphous solid, $\nu_{max}$ (CHCl₃) 3340, 3230, 2100, 1785, 1740, 1686 cm⁻¹.

The total crude product (7) was dissolved in dry dioxan (10 ml) containing lutidine (110 mg) and triphenylphosphine (269 mg). The mixture was heated at 50° for 21 hours and then filtered to remove lutidine hydrochloride. The filtrate was evaporated and the residue dissolved in ethyl acetate. The solution was washed with dilute hydrochloric acid, brine, aqueous sodium bicarbonate, and brine, dried and evaporated. The crude product was chromatographed on silica G to give the pure phosphorane (8) as an amorphous solid $\nu_{max}$ (CHCl$_3$) 3315, 3220, 1755, 1670, 1625 cm$^{-1}$.

EXAMPLE 1 (F)

(3R, 4S)-1-(1'-Butoxycarbonyl-1'-triphenylphosphoranylidene methyl)-3-(phenoxyacetamido)-4-[(2'-oxo)-propyloxy]azetidin-2-one (9)

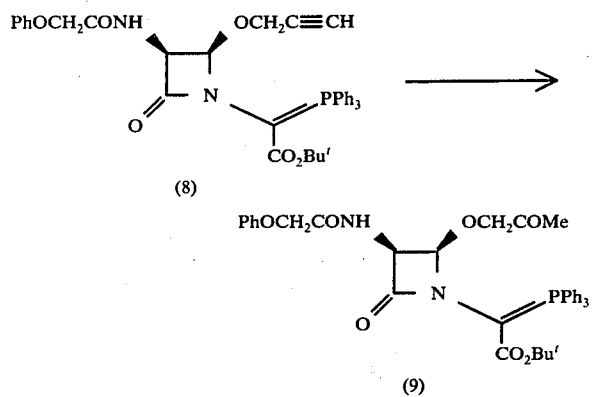

The acetylenic phosphorane (8; 1.77 g) was dissolved in piperidine (15 ml) containing mercuric chloride (1.48 g). After stirring at room temperature for 10 minutes the mixture was poured into ethyl acetate and the solution was washed with dilute hydrochloric acid, until the aqueous layer was acidic. The organic layer was separated, washed with aqueous sodium bicarbonate and brine, dried and evaporated. The product was chromatographed on silica H to give the keto-phosphorane (9; 1.4 g) $\nu_{max}$ (CHCl$_3$) 3300, 1755, 1710, 1670, 1620 cm$^{-1}$.

EXAMPLE 1 (G)

(6R, 7S)-Tert-Butyl 7-phenoxyacetamido-3-methyl-1-oxadethiaceph-3-em-4-carboxylate (10)

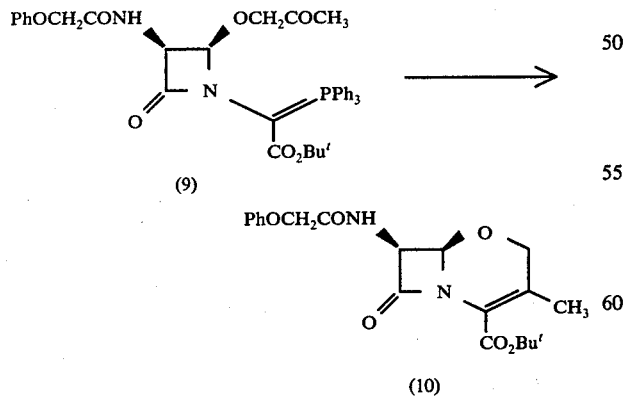

The keto-phosphorane (9; 1.44 g) was refluxed in dry dioxan (50 ml) under nitrogen for 16 hours. The solvent was evaporated and the residue chromatographed on silica H to give the oxa-cephem (10; 664 mg) $[\alpha]_D^{21}$ −39.5° (C=1.38% in CHCl$_3$) $\nu_{max}$ (CHCl$_3$) 3320, 1785, 1707, 1685, 1640 cm$^{-1}$. δ ppm (CDCl$_3$) 1.58 (s, 3H), 2.05 (s, 2H), 4.37 (s, 2H), 4.63 (s, 2H), 5.17 (d, 1H, J=4 Hz), 5.67 (d.d., 1H, J=4 Hz and 9 Hz), 6.9–7.6 (m, 6H). (Found:- M,388.1681, C$_{20}$H$_{24}$N$_2$O$_6$ requires M, 388.1634).

EXAMPLE 1 (H)

(6R, 7S)-7-Phenoxyacetamido-3-methyl-1-oxadethiaceph-3-em-4-carboxylate acid (11)

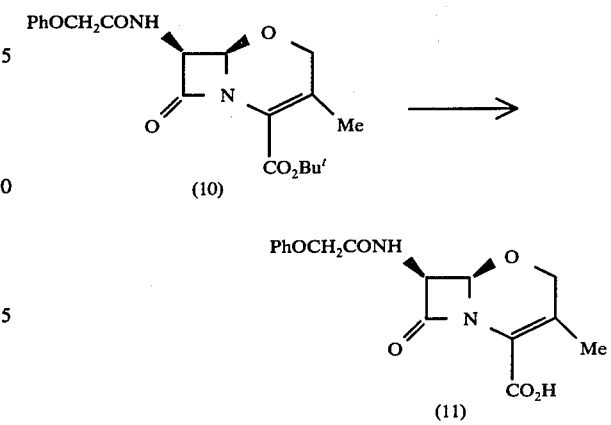

The lactam (297 mg) was dissolved in trifluoroacetic acid (5 ml) and the mixture was kept at room temperature for 10 minutes. The solvent was evaporated and the residue re-evaporated from toluene (x2). The total product was dissolved in ethyl acetate (10 ml) and the solution vigorously stirred with saturated aqueous sodium bicarbonate (8 ml) for 1 hour. The aqueous layer was separated, washed with ethyl acetate and re-separated. The aqueous extract was layered with ethyl acetate, cooled to ca. 5°, and acidified with 2N hydrochloric acid to pH 2, with vigorous stirring. The organic layer was separated, washed with brine, dried and evaporated to give a foam. Trituration with ether afforded the free acid (11; 168 mg) as a pale yellow solid. $[\alpha]_D^{21}$ −39.9° (C= 1.04% in CHCl$_3$) $\nu_{max}$(CHCl$_3$) 3340 (broad), 1782, 1710, (sh), 1685, 1645 cm$^{-1}$. $\nu_{max}$ (KBr) 3400 (broad), 1782, 1710 (sh), 1680, 1640 (sh) cm$^{-1}$, $\lambda_{max}$(EtOH) 263 nm (ε 6,577), δ ppm (CDCl$_3$) 2.1 (s, 3H), 4.43 (s, 2H), 4.67 (s, 2H), 5.23 (d, 1H, J=4 Hz), 5.8 (d.d., 1H, J=4Hz and 9 Hz), 6.8–7.7 (m, 6H), 8.53 (b.s., 1H, exchanged by D$_2$O).

The minimum inhibitory concentrations (MIC) of this compound required to inhibit the growth of various bacteria on nutrient agar are tabulated below:

| Gram-positive bacteria | MIC (μg/ml) |
| --- | --- |
| B. subtilis | 0.05 |
| Staph. aureus Oxford* | 0.25 |
| Staph. aureus Russell | 0.5 |
| β-Haemolytic Strep. CN10 | 0.05 |

| Gram-negative bacteria | MIC (μg/ml) |
| --- | --- |
| Salmonella typhi | 125 |
| Shigella sonnei | 125 |
| Klebsiella aerogenes | 25 |
| Proteus mirabilis C977 | 125 |

*β-Lactamase-producing strain

EXAMPLE 2 (A)

(3R, 4R)-4-(Methylsulphonyl)-3-tritylaminoazetidin-2-one (14)

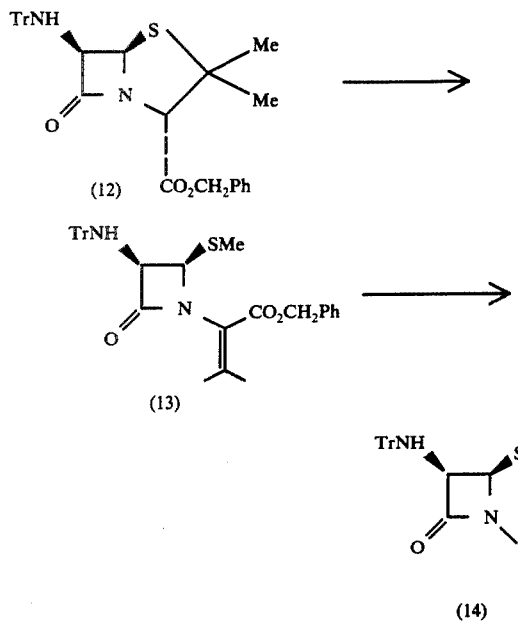

Benzyl 6β-tritylaminopenicillanate [(12); 52 g] was suspended in dry tetrahydrofuran (500 ml). To the suspension was added methyl iodide (15 g) and freshly powdered sodium hydroxide (4.2 g) and the mixture stirred at room temperature for 18 hr.

The solvent was then removed by evaporation in vacuo and the residue dissolved in ethyl acetate and water. The aqueous layer was separated, and the organic layer washed with brine, separated, dried (MgSO₄) and evaporated to give the crude secopenicillin (13) as a pale orange gum (55 g).

Without further purification, the total crude product was dissolved in dimethylformamide (400 ml), acetic acid (40 ml) and water (80 ml) and the resulting solution cooled to −10°.

Powdered potassium permanganate (40 g) was then added portionwise over 10–15 minutes, keeping the temperature below 0°. The mixture was then stirred, at this temperature, for a further 1 hr, after which ethyl acetate and water were added, and then sulphur dioxide was passed into the mixture until all the manganese dioxide had been reduced. The two layers were separated and the organic layer washed successively with water, aqueous sodium bicarbonate, and brine. The dried MgSO₄ organic layer was evaporated to give a pale yellow gum. Chromatography of the crude product on silica gel gave the required azetidinone (14) as an amorphous solic (22 g).

$\nu_{max}$ (CHCl₃) cm⁻¹. 3310, 2975, 1785, 1311, 1138, δ ppm (CDCl₃) 2.66 (s, 3H), 3.53 (d. 1H, J=10 Hz exchanges with D₂O), 4.46 (d. 1H, J=5.7 Hz), 4.73 (d.d., 1H, J=5.7 Hz and 10 Hz;collapses to a doublet J=5.7 Hz on D₂O exchange), 6.90 (s, 1H, exchanges with D₂O), 7.10–7.70 (m, 15H).

EXAMPLE 2 (B)

(3R, 4S)-4-(Progargyloxy)-3-tritylaminoazetidin-2-one (15) and (3S, 4S)-4-(propargyloxy)-3-tritylaminoazetidin-2-one (16)

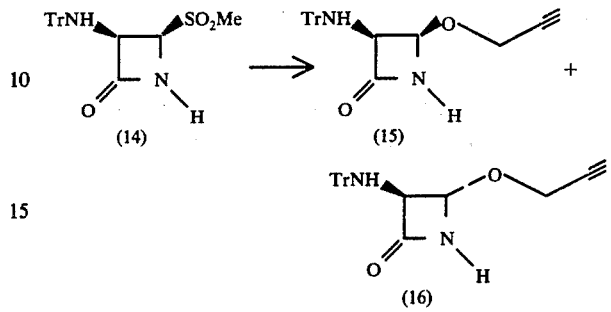

The sulphone [(14; 4.06 g] was heated in dry toluene at 80° with propargyl alcohol (1.68 g) and zinc acetate dihydrate (1.05 g) for 4 hrs. The cooled solution was decanted off and the residual solid triturated with ethyl acetate. These extracts were combined with the toluene fraction and evaporated to give a brown oily residue. Chromatography on silica gel, afforded the cis-isomer (15) as a white amorphous solid (0.478g). $\nu_{max}$ (CHCl₃) cm⁻¹. 3330, 3245, 2970 1772. δ ppm (CDCl₃) 2.40 (t, 1H, J=3 Hz) 3.01 (d, 1H, J=10 Hz exchanges with D₂O), 3.60 and 3.96 (AB qt., 2H, J=15 Hz;each peak is further split into a doublet J=3 Hz), 4.06–4.45 (m, 2H), 6.80 (s, 1H, exchanges with D₂O), 7.20–7.90 (m, 15H). Found:- M, 382.1675; C₂₅H₂₂N₂O₂ requires M, 382.1681. Error 1.6 ppm.

Further elution gave the trans-isomer (16) as a white amorphous solid (0.473 g). $\nu_{max}$ (CHCl₃) cm⁻¹ 3330, 3245, 2970, 1772. δ ppm (CDCl₃) 2.40 (t, 1H, J=2Hz), 2.73 (broad s, 1H, exchanges with D₂O), 3.54 and 3.80 (AB qt., 2H, J=15 Hz each part is further split into a doublet, J=2 Hz), 4.00–4.30 (m, 2H), 6.90–7.70 (m, 16H, reduces to 15H on D₂O exchange).

EXAMPLE 2 (C)

(3R, 4S)-1-(1'-Hydroxy-1'-tert-butoxycarbonylmethyl)-4-(propargyloxy)-3-tritylaminoazetidin-2-one (17)

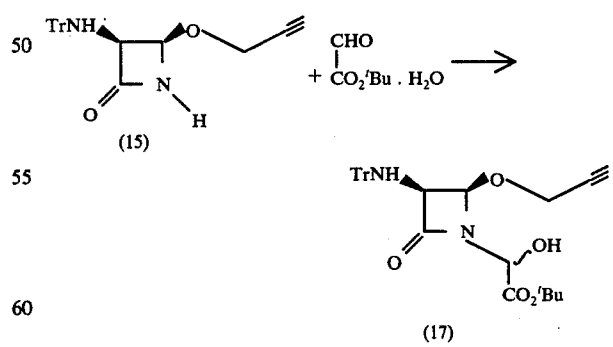

Tert-butylglyoxylate hydrate (1.89 g) was refluxed in dry benzene (25 ml) in a Dean-Stark apparatus to remove any water present, and then the azetidinone (15) (0.515 g) was added in benzene (5 ml) and the mixture refluxed. After 5 hrs. the reaction mixture was cooled, and the solvent evaporated. The residual colourless oil was chromatographed on silica gel to give the hydroxy compound (17) (0.511 g) as a white amorphous solid. $v_{max}$ (CHCl$_3$) cm$^{-1}$. 3400, 3218, 2930, 1770, 1728.

EXAMPLE 2 (D)

(3R, 4S-1-(1'-Tert-Butoxycarbonyl-1'-triphenylphosphoranylidenemethyl)-4-(propargyloxy)-3-tritylaminoazetidin-2-one (19)

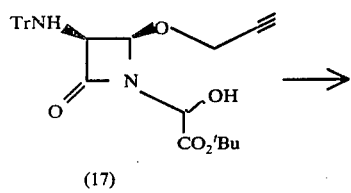

(17)

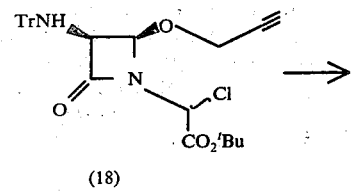

(18)

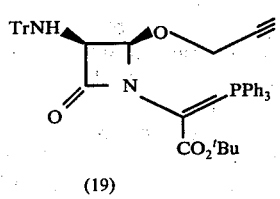

(19)

The hydroxy compound [(17); 0.512 g] was taken up in dry tetrahydrofuran (15 ml) and the solution cooled to −20° and lutidine (0.17 ml) was added. To the stirred solution, at −20°, was added thionyl chloride (0.11 ml) in dry tetrahydrofuran (5 ml), dropwise, over 5 minutes. After a further 15 minutes, the precipitated lutidine hydrochloride was filtered off and washed copiously with toluene. The filtrate and washings were combined and evaporated to give the crude chloride (18).

This crude product was dissolved in dry dioxan (12 ml) and lutidine (0.23 ml), and triphenylphosphine (0.524 g) added. After stirring, under nitrogen, at 55° for 16 hr., the resulting suspension was filtered and the filtrate evaporated. The residue was taken up in ethyl acetate, and washed successively with dilute hydrochloric acid, aqueous sodium bicarbonate and brine. The organic layer was dried (MgSO$_4$) and evaporated to give an oil, which was chromatographed on silica gel. The phosphorane product (19) was obtained as an amorphous solid (0.407 g) $v_{max}$ (CHCl$_3$) cm$^{-1}$ 3230, 2940, 1750 1632.

EXAMPLE 2 (E)

(3R, 4S)-1-(1'-Tert-Butoxycarbonyl-1'-triphenylphosphoranylidenemethyl)-4-(2'-oxopropyloxy)-3-tritylaminoazetidin-2-one (20)

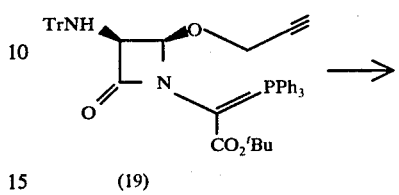

(19)

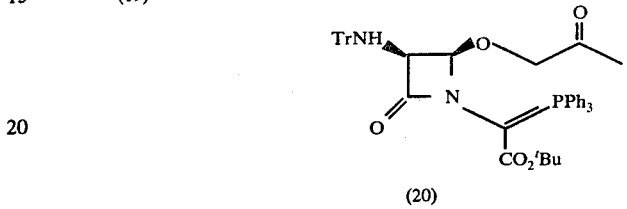

(20)

The acetylenic phosphorane (19; 0.4 g) was dissolved in piperidine (6 ml) and mercuric chloride (0.287 g) added. The mixture was stirred at room temperature for 1¼ hr. when the solvent was removed by evaporation. The residue was taken up in ethyl acetate and washed with hydrochloric acid, aqueous sodium bicarbonate, and then brine. The organic layer was dried (MgSO$_4$) and evaporated to an oily residue which was chromatographed on silica gel to afford the required keto-phosphorane (20) as a white amorphous solid (0.258 g) $v_{max}$ (CHCl$_3$) cm$^{-1}$ 2950, 1756, 1712, 1630.

EXAMPLE 2 (F)

(6R, 7S)-Tert-Butyl 7-tritylamino-3-methyl-1-oxadethiaceph-3-em-4-carboxylate

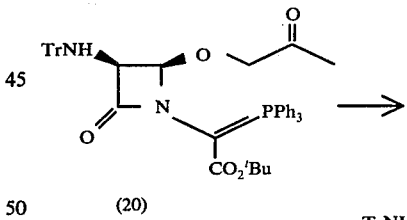

(20)

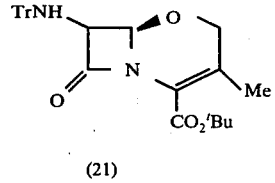

(21)

The keto-phosphorane (20; 0.258 g) was dissolved in dry dioxan (10 ml) and the solution was gently refluxed for 16 hrs. After this time, the solvent was removed and the residue chromatographed on silica gel to give the oxacephem (21) as an amorphous solid (0.165 g). $v_{max}$ (CHCl$_3$) cm$^{-1}$. 2900, 1780, 1710. δ ppm (CDCl$_3$) 1.52 (s, 9H), 1.91 (s, 3H), 3.13 (d, 1H, J=11Hz exchanges with D$_2$O), 3.86 (d, 1H, J=4 Hz), 4.06 (s, 2H), 4.30 (dd, 1H, J=4 Hz and 11 Hz collapses to doublet J=4 Hz on D$_2$O exchange), 7.10–7.80 (m, 15H).

EXAMPLE 2 (G)

(6R, 7S)-Tert-butyl 7-[D-α-phenylglycyl]amino-3-methyl-1-oxadethiaceph-3-em-4-carboxylate (23)

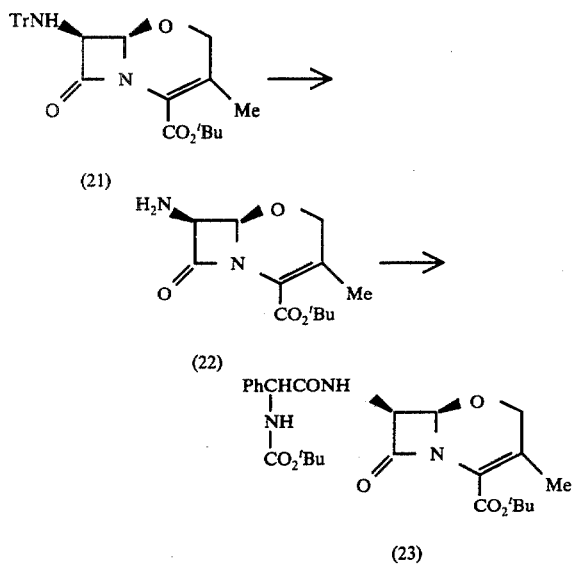

The trityl cephem (21; 0.130 g) was dissolved in dry methylene chloride (8 ml) and cooled to −20°, and p-toluenesulphonic acid hydrate (54 mgs) in the minimum volume of methanol was added dropwise. The solution was then left at 0° for 16 hrs. when the solvent was removed, and the residue diluted with ethyl acetate and aqueous sodium bicarbonate. The organic layer was separated, and washed with brine, dried (MgSO$_4$) and evaporated to give the crude free amino compound (22) as a light brown oil.

To methyl chloroformate (0.027 g) in dry tetrahydrofuran (9 ml), cooled to −20°, was added, dropwise over 5 minutes, a solution of N-(t-butoxycarbonyl)-D-α-phenylglycine (0.071 g), triethylamine (0.029 g) and dibenzylamine (1 drop), in dry tetrahydrofuran (5 ml). After 20 minutes, the amino compound (22) was added, dropwise in dry tetrahydrofuran (4 ml) over 5 minutes, and the mixture stirred at −20° for a further 2 hrs and then for 1 hr. at 0°. The mixture was then filtered, and the triethylamine hydrochloride washed copiously with ethyl acetate. The filtrate and washings were evaporated and the residue taken up in ethyl acetate and washed with 5% aqueous sodium bicarbonate, and brine. The organic layer was separated, dried (MgSO$_4$) and evaporated to a gum, which after silica gel chromatography gave the required product (23) as an amorphous solid (52 mg). $\nu_{max}$ (CHCl$_3$) cm$^{-1}$. 3415, 1792, 1711, 1708, 1695, 1650 (sh). δ ppm (CHCl$_3$) 1.45 (s, 9H), 1.57 (s, 9H), 2.01 (s, 3H), 4.21 (s, 2H), 5.03 (d, 1H, J=4 Hz), 5.30 (d, 1H, J=7Hz), 5.65 (dd, 1H, J=4 Hz and 10Hz), 5.80 (d, 1H, J=7 Hz), 6.93 (d, 1H, J=10Hz), 7.48 (s, 5H).

EXAMPLE 2 (H)

(6R, 7S)-7-[D-α-Phenylglycyl]amino-3-methyl-1-oxadethiaceph-3-em-4-carboxylic acid, trifluoroacetic acid salt (24)

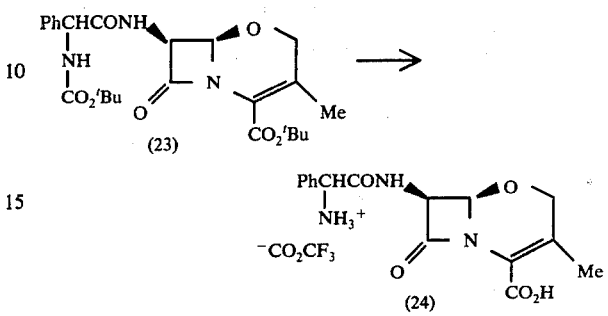

The oxa-cephem ester (23; 52 mg) was dissolved in neat trifluoroacetic acid (1 ml) and allowed to stand at room temperature for 7 minutes. The solvent was then removed, and the residue re-evaporated (x3) from toluene. Trituration of the production with ether gave the free acid (24) as an off-white solid (36 mg). $\nu_{max}$ (KBr disc) cm$^{-1}$ 3440 (broad), 3000 (broad), 1770, 1680 (broad), 1630 (sh). Optical rotation $[\alpha]_D^{21} = -6.41°$ (0.6% in MeOH).

EXAMPLE 2 (I)

(6R, 7S)-Tert-Butyl 7-(D-Mandelyl)amino-3-methyl-1-oxodethia-ceph-3-em-4-carboxylate (25)

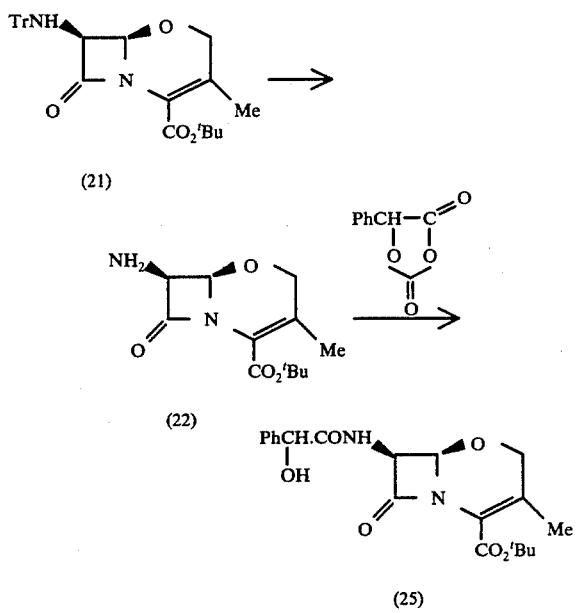

The oxa-cephem (21; 200 mg) was detritylated as described in Example 2 (G) and the crude amino compound (22), was dissolved in dry methylene chloride (6 ml) and cooled to −20°. D-Mandelyl O-carboxyanhydride (79 mg. 1.1 eq.) was added, and the mixture stirred at −20° for 1 hr. The reaction mixture was washed with dilute aqueous sodium bicarbonate solution, and brine, and the organic layer dried (MgSO$_4$), and evaporated to an oil.

Chromatography on silica gel gave the acylamino oxa-cephem (25; 106 mg) as a white amorphous solid. $v_{max}$ (CHCl$_3$) 3320, 1787, 1710, 1683, 1650 (sh) cm$^{-1}$. δ ppm (CDCl$_3$) 1.55 (s, 9H), 2.00 (s, 3H), 4.30 (broadened s, 3H. On D$_2$O exchange, collapses to sharp singlet, 2H), 5.07 (d, 1H, J=4Hz), 5.17 (s, 1H,), 5.53 (dd, 1H, J=4 and 10 Hz.On D$_2$O exchange, collapses to a doublet J=4 Hz), 7.47 (s, 5H), 7.53 (d, 1H, J=10 Hz exchanged with D$_2$O). (Found: M, 388.1610; C$_{20}$H$_{24}$N$_2$O$_6$ requires M, 388.1634)

EXAMPLE 2 (J)

(6R, 7S)-7-(D-Mandelyl)amino-3-methyl-1-oxadethia-ceph-3-em-4-carboxylic acid (26)

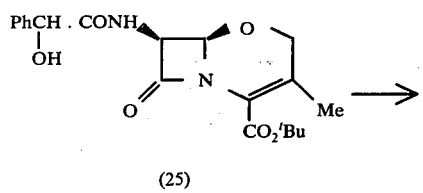

(25)

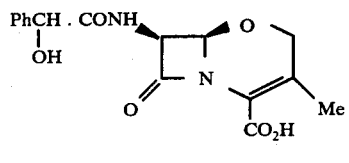

(26)

The oxa-cephem ester (25; 64 mg) was dissolved in neat trifluoroacetic acid (1 ml) at room temperature, and the solution was left for 6 minutes. The solvent was then evaporated, and the residue twice taken up in dry toluene, and re-evaporated to dryness. The residue upon trituration with ether gave the oxa-cephem free acid (26) as a buff solid (26; 46mg). [α]$_D^{22}$ = −39.87° (C= 0.8% in MeOH). $v_{max}$ (KBr) 3400 (b), 1771, 1660 (b) cm$^{-1}$ λ$_{max}$ (EtOH) 260 nm. ($\epsilon_m$ = 4,160).

The minimum inhibitory concentrations (MIC) of this compound required to inhibit the growth of various bacteria on nutrient agar are tabulated below:

| Gram-positive bacteria | MIC (μ/ml) |
| --- | --- |
| B. subtilis | 0.1 |
| Staph. aureus aureus Oxford | 2.5 |
| Staph. aureus Russell* | 25 |
| β-Haemolytic Strep. CN10 | 0.05 |
| Gram-negative bacteria | |
| E. coli JT1 | 5 |
| Salmonella typhi | 5 |
| Shigella sonnei | 5 |
| Klebsiella aerogenes A | 5 |

*β-Lactamase-producing strain

EXAMPLE 2 (K)

(6R, 7S)-Tert-Butyl 7-(2'-thienylacetamido)-3-methyl-1-oxadethia-ceph-3-em-4-carboxylate (27)

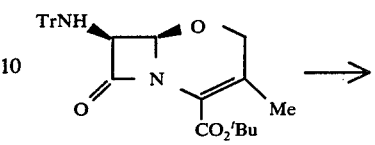

(21)

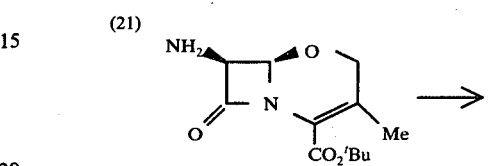

(22)

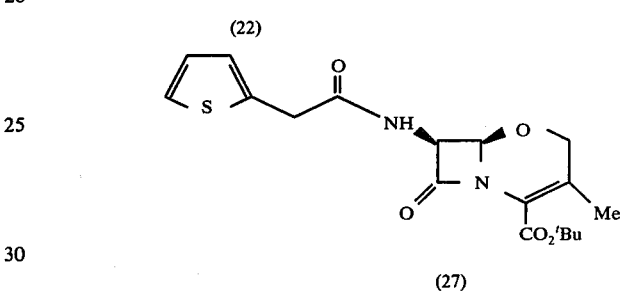

(27)

The tritylamino oxa-cephem (21; 150 mg) was detritylated as in Example 2 (G) and the crude amino compound (22) dissolved in dry methylene chloride (5ml) and cooled to −20°. To this solution was added triethylamine (0.084 ml) followed by dropwise addition over 2 minutes of freshly distilled 2-thienyl acetyl chloride (53 mg) in dry methylene chloride (2 ml).

After 5 minutes, the reaction mixture was poured into water, the organic layer separated and dried (MgSO$_4$), and evaporated to an oil. Chromatography of the residue on silica gel gave the acylamino derivative (27, 51 mg) as a white solid. $v_{max}$ (CHCl$_3$) 3330, 1787, 1710, 1683, 1640 (sh) cm$^{-1}$. δ ppm (CDCl$_3$) 1.53 (s, 9H), 2.01 (s, 3H), 3.92 (s, 2H), 4.30 (s, 2H), 5.06 (d, 1H, J=4 Hz), 5.68 (dd, 1H, J=4 and 9 Hz), 6.70 (d, 1H, J=9 Hz exchanges with D$_2$O), 7.00–7.55 (m, 3H).

EXAMPLE 2 (L)

(6R, 7S)-7-(2-Thienylacetamido)-3-methyl-1-oxadethia-ceph-3-em-4-carboxylic acid (28)

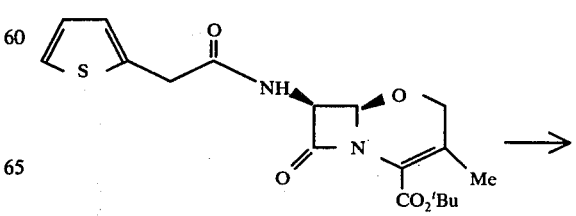

(27)

-continued

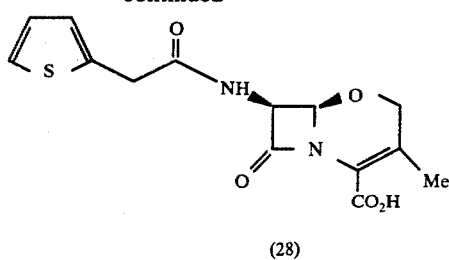
(28)

The oxa-cephem ester (27, 51 mg) was dissolved in neat trifluoroacetic acid (1 ml) and the solution left at room temperature for 5 mins. The solvent was then evaporated, and the residue twice taken up in dry toluene and evaporated to dryness. The free acid (28) was obtained as a pale brown solid (30 mg) upon trituration with ether. $[\alpha]_D^{22} = +2.74°$ (C= 0.8% in MeOH). $\nu_{max}$ (KBr) 3200 (broad), 1775, 1715 (broad), 1650 (broad) cm$^{-1}$. $\lambda_{max}$(EtOH), 236 nm. ($\epsilon_m$ = 10,260).

This compound inhibited B. subtilis at 1 μg/ml, Staph. aureus Oxford at 5 μg/ml, and β-Haemolytic Strep. CN.10 at 5 μg/ml.

EXAMPLE 2 (M)

(6R, 7S)-Tert-Butyl 7-(α-phenoxycarbonylphenylacetamido)-3-methyl-1-oxadethia-ceph-3-em-4-carboxylate (29)

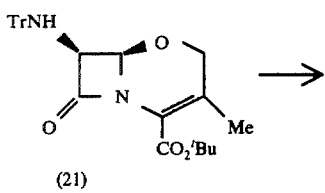
(21)

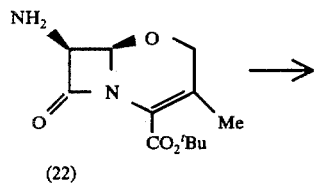
(22)

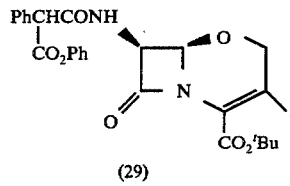
(29)

The mono phenyl ester of phenylmalonic acid (0.256 g) was refluxed in dry benzene (3 ml) with thionyl chloride (0.130 g) for 1 hr. The solvent was then removed and the residue twice taken up in dry toluene and evaporated to give the crude acid chloride as an oil (0.276 g). $\nu_{max}$(CHCl$_3$) 3000, 1810, 1750 cm$^{-1}$.

The crude amino oxo-cephemester (22), obtained as in Example 2 (G) by detritylation of the tritylaminooxacephem (21, 150 mg), was dissolved in dry methylene chloride (6 ml), and cooled to −20°, when triethylamine (0.084 ml) was added. To this solution the crude acid chloride (150 mg.) in dry methylene chloride was added dropwise over a few minutes.

The reaction mixture was then washed with water, the organic layer separated, dried (MgSO$_4$) and evaporated to an oil. Chromatography on silica gel, gave the required acylaminoderivative (29) as a white amorphous solid (81 mg). $\nu_{max}$ (CHCl$_3$) 3270, 1788, 1720, 1710, 1685, 1640 (sh) cm$^{-1}$. δ ppm (CDCl$_3$) 1.55 (s, 9H), 2.00 (s, 3H), 4.30 (s, 2H), 4.93 (s, 1H), 5.07 (d, 1H, J=4 Hz), 5.70 (dd, 1H, J=4 Hz and 9 Hz), 7.0-8.0 (m, 11H, on D$_2$O exchange, reduced to 10H).

EXAMPLE 2 (N)

(6R, 7S)-7-(α-Phenoxycarbonylphenylacetamido)-3-methyl-1-oxadethia-ceph-3-em-4-carboxylic acid (30)

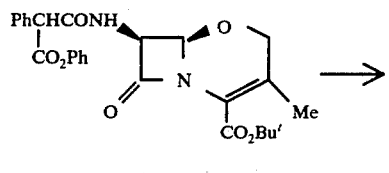
(29)

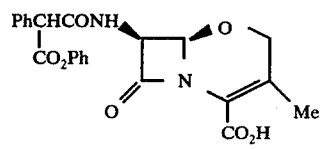
(30)

The acylaminooxa-cephem ester (29) (81 mg) was dissolved in neat trifuloroacetic acid (1 ml) and left at room temperature for 4 minutes. The solvent was then removed, and the residue twice taken up in dry toluene, and evaporated to dryness. Trituration with ether gave the free acid (30) as a light brown solid (32 mg). $[\alpha]_D^{22} = +4.37°$ (C= 0.8% in MeOH). $\nu_{max}$ (KBr) 3400 (broad), 1760, 1660 cm$^{-1}$. $\lambda_{max}$ (EtOH) 259 nm. ($\epsilon_m$= 3,830).

EXAMPLE 3 (A)

(3R, 4S)-4-(2′-Methylallyloxy)-3-tritylaminoazetidin-2-one (31) and (3S, 4S) 4-(2′-Methylallyloxy)-3-tritylaminoazetidin-2-one (32)

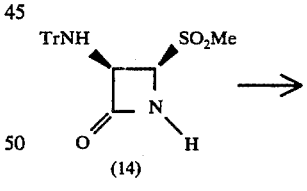
(14)

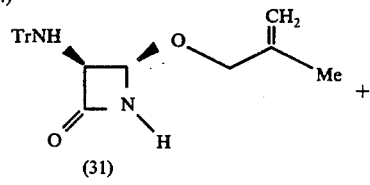
(31)

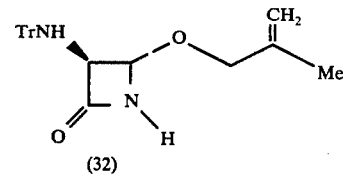
(32)

The sulphone (11; 4.6 g) was heated in dry toluene (50 ml) at 80° with methallyl alcohol (2.16 g; 3 eq.) and zinc acetate dihydrate (1.1 g; 0.5 eq.) for 7 hours. The cooled solution was decanted, and the residual solid triturated with ethyl acetate. These extracts were combined with the toluene fraction, and evaporated to afford a brown oily residue. Chromatography on silica gel afforded the cis-isomer (31; 874 mg) $\nu_{max}$ (CHCl$_3$) 3330, 1765, 1650 cm$^{-1}$. δ ppm (CDCl$_3$). 1.65 (s, 3H), 3.0 (bs, 1H, exchanged with D$_2$O), 3.4 (s, 2H), 4.13 (d, 1H, J=4 Hz), 4.27 (d, 1H, J=4 Hz), 4.88 (s, 2H), 6.47 (bs, 1H, exchanged with D$_2$O), 7.03–7.67 (m, 15H).

Further elution gave the trans-isomer (32) as a white amorphous solid (668 mg). $\nu_{max}$ (CHCl$_3$) 3330, 1765, 1650 cm$^{-1}$. δ ppm (CDCl$_3$) 1.63 (s, 3H), 2.82 (s, 1H, exchanged with D$_2$O), 3.48 (slightly broadened singlet, 2H), 4.13 (s, 1H), 4.27 (s, 1H), 4.88 (s, 2H), 7.03–7.67 (m, 15H).

EXAMPLE 3 (B)

(3R, 4S)-4-(2'-Oxopropyloxy)-3-tritylaminoazetidin-2-one (33)

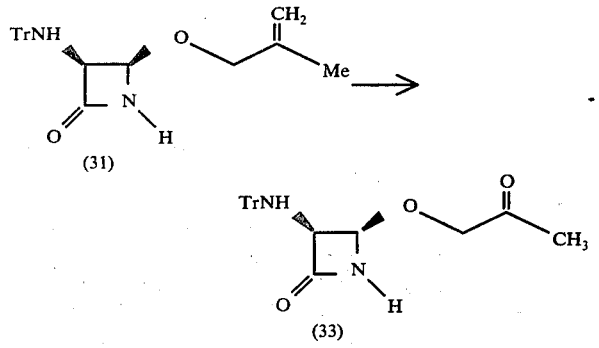

The azetidinone (31; 120 mg) was dissolved in ethyl acetate (5 ml) and the solution cooled to −76°. Ozonised oxygen was passed through the solution until t.l.c. showed no starting material (5 min). Dry nitrogen was bubbled through the solution at −76° for 30 minutes and then triphenylphosphine (85 mg) was added and the solution allowed to reach ambient temperature. After one hour the solvent was evaporated and the residue chromatographed on silica gel to give the ketone (33) as an amorphous solid (95 mg). $\nu_{max}$ (CHCl$_3$) 3330, 1765, 1725 cm$^{-1}$. δ ppm (CDCl$_3$), 1.98 (s, 3H), 3.02 (d, 1H, J=10 Hz, exchanged with D$_2$O), 3.42 and 3.62 (centres of ABq, 2H, J=18 Hz), 4.07 (d, 1H, J=4 Hz), 4.3 (dd, 1H, J=4 Hz and 10 Hz, collapses to doublet J=4 Hz on D$_2$O exchange), 6.9 (bs, 1H, exchanged with D$_2$O), 7–8 (m, 15H).

EXAMPLE 3 (C)

(3R, 4S)-1-(1'-Hydroxy-1'-tert-butoxycarbonylmethyl)-4-(2'-methylallyloxy)-3-tritylaminoazetidin-2-one (34)

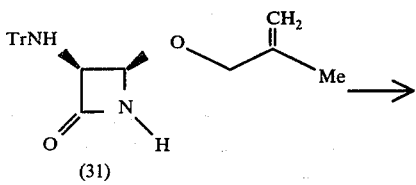

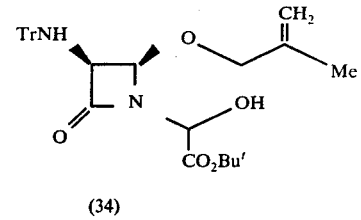

Tert-butylglyoxylate hydrate (1.58 g) was refluxed in benzene (20 ml) in a Dean-Stark apparatus to remove any water present, and then the azetidinone (31; 796 mg) added in benzene (5 ml). The solution was refluxed for a further 5 hours and then the solvent was evaporated. Chromatography on silica gel afforded the hydroxy-compound (34) as a white amorphous solid (972 mg). $\nu_{max}$ (CHCl$_3$) 3400, 3300, 1765, 1730, 1650 cm$^{-1}$.

EXAMPLE 3 (D)

(3R, 4S)-1-(1'-Hydroxy-1'-tert-butoxycarbonylmethyl)-4-(2'-oxopropyloxy)-3-tritylaminoazetidin-2-one (35)

Route I

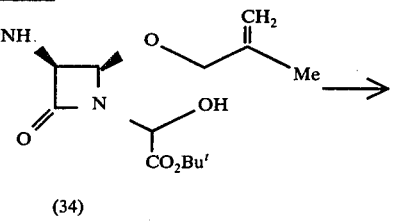

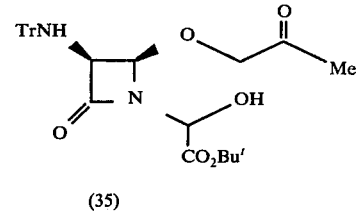

The hydroxy-azetidinone (34; 573 mg) was dissolved in dry ethyl acetate (10 ml) and the solution was cooled to −76°, Ozonised oxygen was passed through the solution until t.l.c. showed no starting material (25 min.). Nitrogen was then bubbled through the solution for 30 minutes and triphenylphosphine (312 mg) added. The reaction mixture was allowed to warm to room temperature and after 1 hour the solvent was evaporated and the product chromatographed on silica. The ketone (35) was isolated as an amorphous solid (470 mg.). $\nu_{max}$ 3400, 3300, 1770, 1730, 1710 (shoulder) cm$^{-1}$.

Route II

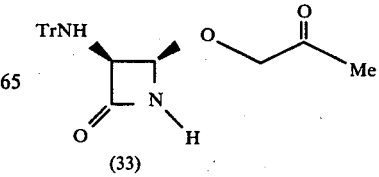

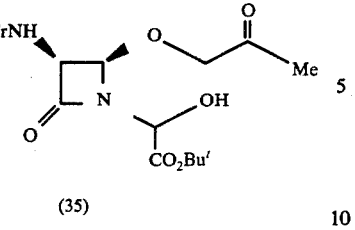

(35)

Tert-butylglyoxylate hydrate (740 mg) was refluxed in benzene (10 ml) in a Dean-Stark apparatus to remove any water present. The azetidinone (33; 396 mg) in benzene (5 ml) was added to the cooled solution, and then the mixture was refluxed for 3 hours. The solvent was evaporated and the residue chromatographed on silica gel to give the ketone (35; 430 mg) as an amorphous solid. $\nu_{max}$ 3400, 3300, 1770, 1730, 1710 (shoulder) cm$^{-1}$.

EXAMPLE 3 (E)

(3R, 4S)-1-(1'-Tert-Butoxycarbonyl-1'-triphenylphosphoranylidenemethyl)-4-(2'-oxopropyloxy)-3-tritylaminoazetidin-2-one (20)

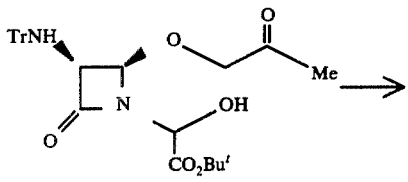

(35)

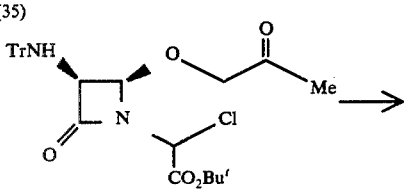

(36)

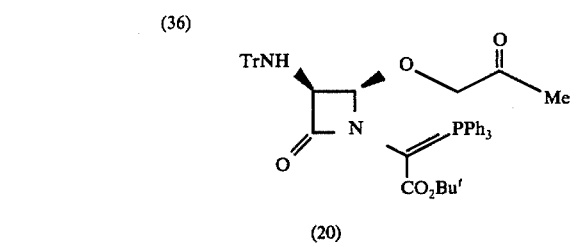

(20)

The alcohol (35; 205 mg) was dissolved in dry tetrahydrofuran (10 ml) and the solution cooled to −20°. Lutidine (64 mg) was added, followed by the dropwise addition of thionyl chloride (69 mg) in dry tetrahydrofuran (1 ml). After 15 minutes, the precipitated lutidine hydrochloride was filtered, the solid being washed copiously with dry toluene. The filtrate and washings were combined and evaporated to give the crude chloride (36).

The total crude chloride (36) was dissolved in dry dioxan (10 ml), and lutidine (84 mg), and triphenylphosphine (202 mg) added. The mixture was stirred under nitrogen at 50°, for 20 hours. The resulting suspension was filtered and the filtrate evaporated. The residue was taken up in ethyl acetate, and washed successively with dilute hydrochloric acid, aqueous sodium bicarbonate, and brine. The organic layer was dried and evaporated and the residue chromatographed on silica gel. The ketophosphorane (20) was isolated as an amorphous solid (160 mg). $\nu_{max}$ 1756, 1712, 1630 cm$^{-1}$.

EXAMPLE 3 (F)

(6R, 7S)-Tert-Butyl 7-tritylamino-3-methyl-1-oxadethiaceph-3-em-4-carboxylate (21)

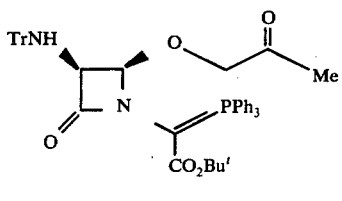

(20)

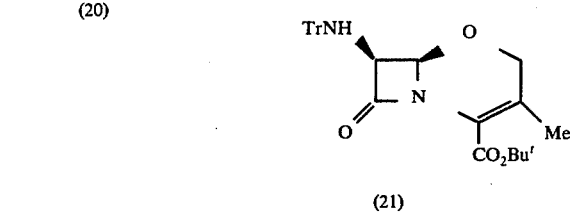

(21)

The keto-phosphorane from Example 3 (E) (20; 160 mg) was dissolved in dry dioxan (10 ml) and the solution was gently refluxed under nitrogen for 7 hours. The solvent was evaporated and the residue chromatographed on silica gel to give the oxa-cephem (21) as an amorphous solid (80 mg). The product was identical to that described in Example 2 (F). (N.M.R., I.R., T.L.C.)

EXAMPLE 4 (A)

(3R, 4S)-4-(2'-Benzyl-3'-methoxycarbonylallyloxy)-3-tritylaminoazetidin-2-one (37) and (3S, 4S)-4-(2'-Benzyl-3'-methoxycarbonylallyloxy)-3-tritylamino azetidin-2-one (38)

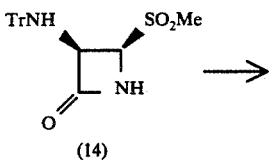

(14)

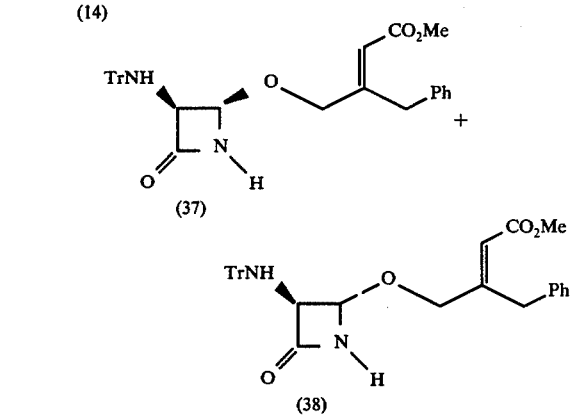

The sulphone (14; 3.4 g) was heated in dry toluene (20 ml) at 80° with (E)-2-benzyl-3-hydroxy-1-methoxycarbonylprop-1-ene (1.75 g; 2 eq.) and zinc acetate dihydrate (465 mg; 0.5 eq) for 8 hours. The cooled solution was decanted, and the residual solid triturated with ethyl acetate. These extracts were combined with the toluene fraction and evaporated to give a brown oily residue. Chromatography on silica gel afforded the cis-isomer (37; 274 mg). $\nu_{max}$ (CHCl$_3$) 3320, 1775, 1715, 1657 cm$^{-1}$. δ ppm (CDCl$_3$) 2.52 (b.s., 1H, exchanged with D$_2$O), 3.47 (d, 2H, J=~1 Hz), 3.73 (s, 3H), 3.75-4.4 (m, 2H), 4.68 (s, 2H), 5.87 (b.s., 1H), 6.38 (b.s. 1H, exchanged by D$_2$O), 7.0-7.9 (m, 20H) (Found:- M, 532.2325 C$_{34}$H$_{32}$N$_2$O$_4$ requires M, 532.2362)

Further elution provided the trans-isomer (38; 218 mg). $\nu_{max}$ (CHCl$_3$) 3320, 1775, 1715, 1657 cm$^{-1}$. δ ppm (CDCl$_3$) 2.98 (3, 1H, exchanged with D$_2$O), 3.42 (b.s. 2H), 3.75 (s, 3H), 3.77-4.3 (m, 2H), 4.67 (s, 2H), 5.9 (b.s. 1H), 7.03 (b.s. 1H, exchanged with D$_2$O), 7.1-8.0 (m, 20H).

EXAMPLE 4 (B)

(3R, 4S)-1-(1'-Hydroxy-1'-tert-butoxycarbonylmethyl)-4-(2'-benzyl-3'-methoxycarbonylallyloxy)-3-tritylaminoazetidin-2-one (39)

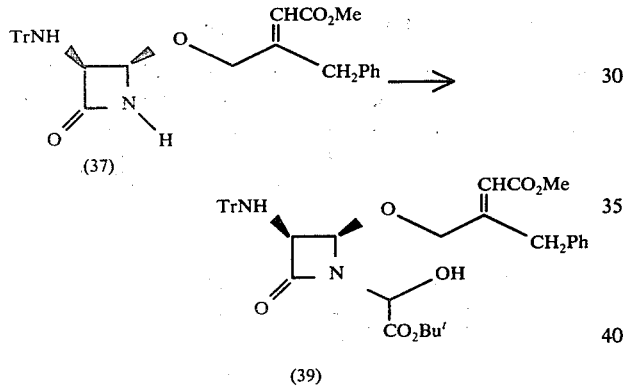

Tert-butylglyoxylate hydrate (1.9 g) was refluxed in benzene (30 ml) in a Dean-Stark apparatus to remove any water present, and then the azetidinone (37; 701 mg) was added in benzene (5 ml). The solution was refluxed for 3 hours and then the solvent was evaporated. Chromatography on silica gel afforded the hydroxy-compound (39) as a white amorphous solid (492 mg). $\nu_{max}$ (CHCl$_3$) 3400, 1770, 1728, 1715, 1650 cm$^{-1}$.

EXAMPLE 4 (C)

(3R, 4S)-1-(1'-Hydroxy-1'-tert-butoxycarbonylmethyl)-4-(2'-oxo-3'-phenylpropyloxy)-3-tritylaminoazetidin-2-one (40)

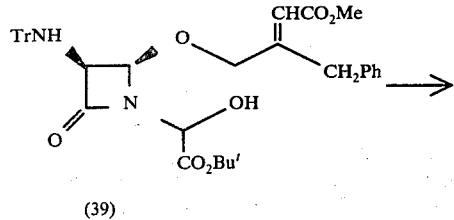

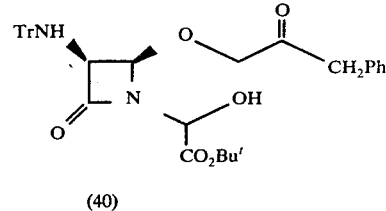

The azetidinone (39; 260 mg) was ozonised in ethyl acetate (10 ml) at −76° until t.l.c. showed no starting material (5 min). Nitrogen was then bubbled through the solution for 30 minutes and triphenylphosphine (150 mg) added. The reaction mixture was allowed to warm to room temperature and after 4 hours the solvent was evaporated and the product chromatographed on silica. The ketone (40) was isolated as an amorphous solid (230 mg). $\nu_{max}$ (CHCl$_3$) 3400, 1770, 1730, 1720 (sh) cm$^{-1}$.

EXAMPLE 4 (D)

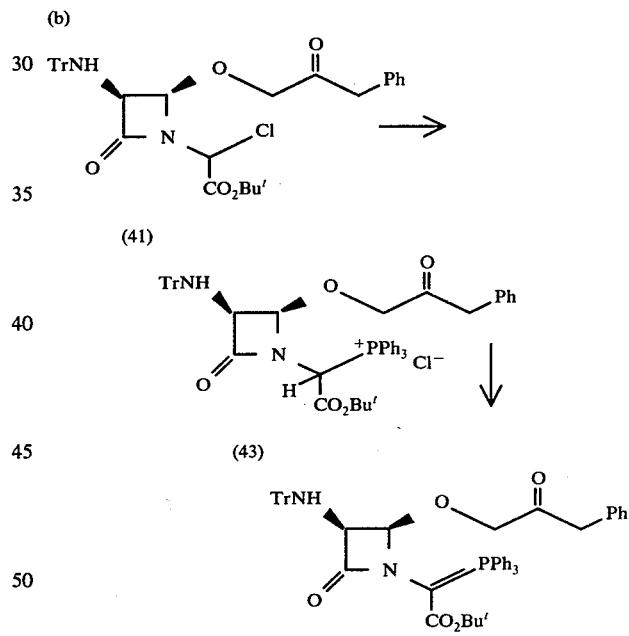

The chloro-ketone (41; 90 mg: obtained as in part (a) by chromatography of the crude chloride on silica gel) was dissolved in dry dioxan (5 ml) and triphenylphosphine (120 mg) was added. The solution was heated at 55° under nitrogen for 24 hours to provide the phosphonium salt (43), and was then cooled to room temperature. Lutidine (25 mg) was added and the reaction mixture stirred for 30 minutes. Work-up as in part (a) afforded the crude product which was chromatographed on silica gel to give the pure phosphorane (42; 65 mg).

EXAMPLE 4 (E)

(6R, 7S)-Tert-Butyl 7-tritylamino-3-benzyl-1-oxadethiaceph-3-em-4-carboxylate

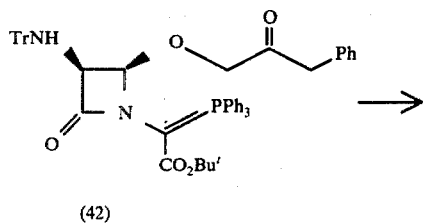

(42)

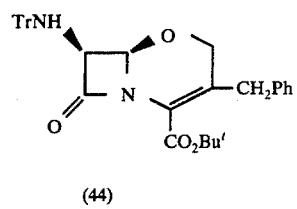

(44)

The keto-phosphorane (42; 105 mg) was refluxed in dry toluene (10 ml) under nitrogen for 9 hours. The solvent was evaporated and the residue chromatographed on silica gel to afford the oxa-cephem (44; 50 mg). $\nu_{max}$(CHCl$_3$) 3260 (weak), 1780, 1710, 1638 cm$^{-1}$. $[\alpha]_D^{21}$ −59.4 (C=1.05 in chloroform) δ ppm (CDCl$_3$) 1.55 (s, 9H), 3.1 (d, 1H, J=12 Hz exchanged by D$_2$O), 3.48 and 4.02 (centres of ABq, 2H, J=16 Hz), 3.95 (s, 2H), 4.02 (d, 1H, J=3.5 Hz), 4.35 (dd, 1H, J=3.5 Hz and 12 Hz, collapses to d, J=3.5 Hz on D$_2$O exchange), 7.2–7.9 (m, 20H).

EXAMPLE 4 (F)

(6R, 7S)-Tert-Butyl 7-(D-mandelyl)amino-3-benzyl-1-oxadethiaceph-3-em-4-carboxylate (46)

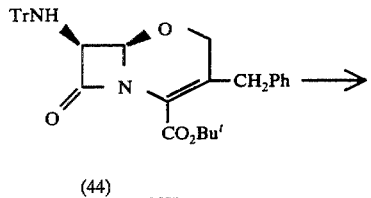

(44)

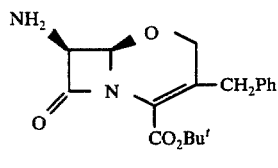

(45)

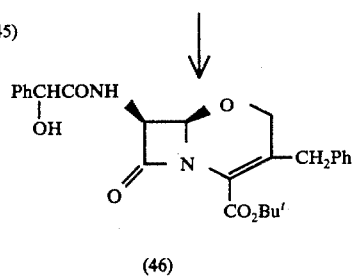

(46)

The oxa-cephem (44; 55 mg) was dissolved in methylene chloride (3 ml) and the solution cooled to −20°. p-Toluene sulphonic acid monohydrate (18 mg) was then added in methanol (0.5 ml) and the reaction mixture left at 0° for 16 hours. The solution was washed with dilute aqueous sodium bicarbonate, brine, dried and evaporated to afford the free base (45).

The total crude product from the de-tritylation was dissolved in dry methylene chloride (3 ml) at −20° and D-mandelyl O-carboxyanhydride (18 mg) added. After 3 hours the solution was washed with dilute aqueous sodium bicarbonate, brine, dried and evaporated. The crude product was chromatographed on silica to give the acylamino-derivative (46; 41 mg). $\nu_{max}$ (CHCl$_3$) 3315, 1785, 1705, 1685, 1640 cm$^{-1}$. δ ppm (CDCl$_3$) 1.57 (s, 9H), 3.58 and 4.18 (centres of ABq, 2H, J=16 Hz), 3.72 (d, 1H, exchanged by D$_2$O), 4.25 (s, 2H), 5.05 (d, 1H, J=4 Hz), 5.12 (d, 1H), 5.58 (q, 1H, J=4 Hz and 9 Hz).

EXAMPLE 4 (G)

(6R, 7S)-7-(D-Mandelyl)amino-3-benzyl-1-oxadethiaceph-3-em-4-carboxylic acid (47)

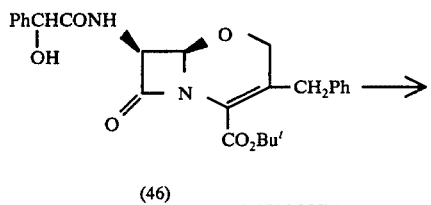

(46)

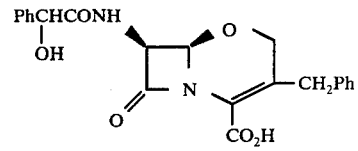

(47)

The oxa-cephem ester (46; 39 mg) was dissolved in neat trifluoroacetic acid (1 ml) at room temperature, and the solution was left for 5 minutes. The solvent was then evaporated, and the residue twice taken up in dry toluene, and re-evaporated to dryness. The residue slowly solidified on trituration with ether (x2) to give the oxa-cephem free acid (47) as a pale yellow solid (15 mg). $\nu_{max}$(CHCl$_3$) 3310, 2200–3000 (broad), 1785, 1720, 1680, 1640 cm$^{-1}$.

We claim:

1. A compound of the formula

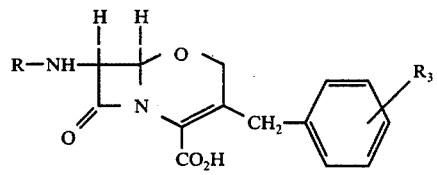

wherein R is D-α-hydroxy-benzylcarbonyl and R$_3$ is hydrogen, carboxylic acid, carboxamido or an esterified carboxylic acid of 1–10 carbons in the ester portion.

2. The compound of claim 1 wherein R$_3$ is hydrogen.

3. The compound of claim 2 which is (6R, 7S)-7-(D-mandelyl)amino-3-benzyl-1-oxadethiaceph-3-em-4-carboxylate or a pharmaceutically acceptable salt thereof.

4. The compound of claim 1 which is (6R, 7S)-7-(D-mandelyl)amino-3-benzyl-1-oxadethiaceph-3-em-4-carboxylic acid.

5. A pharmaceutical composition useful for treating bacterial infections in humans and animals which comprises an antibacterially effective amount of a compound of the formula

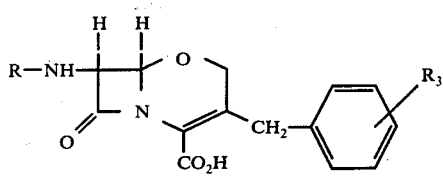

or a pharmaceutically acceptable salt thereof wherein R is D-α-hydroxy-benzylcarbonyl and $R_3$ is hydrogen, carboxylic acid, carboxamido or an esterified carboxylic acid of 1–10 carbons in the ester portion, in combination with a pharmaceutically acceptable carrier.

6. The composition of claim 5 wherein $R_3$ is hydrogen.

7. The composition of claim 6 wherein the compound is (6R, 7S)-7-(D-mandelyl)amino-3-benzyl-1-oxadethiaceph-3-em-4-carboxylate or a pharmaceutically acceptable salt thereof.

8. The composition of claim 5 wherein the compound is (6R, 7S)-7-(D-mandelyl)amino-3-benzyl-1-oxadethiaceph-3-em-4-carboxylic acid.

9. A method of treating bacterial infections in humans and animals which comprises administering to said human or animal in need thereof an antibacterially effective amount of a compound of the formula

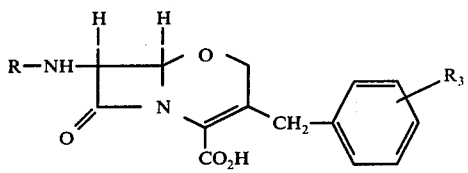

or a pharmaceutically acceptable salt thereof wherein R is D-α-hydroxy-benzylcarbonyl and $R_3$ is hydrogen, carboxylic acid, carboxamido or an esterified carboxylic acid of 1–10 carbons in the ester portion.

10. The method of claim 9 wherein $R_3$ is hydrogen.

11. The method of claim 10 wherein the compound is (6R, 7S)-7-(D-mandelyl)amino-3-benzyl-1-oxadethiaceph-3-em-4-carboxylate or a pharmaceutically acceptable salt thereof.

12. The method of claim 9 wherein the compound is (6R, 7S)-7-(D-mandelyl)amino-3-benzyl-1-oxadethiaceph-3-em-4-carboxylic acid.

* * * * *